United States Patent
Tacha

(10) Patent No.: US 6,580,056 B1
(45) Date of Patent: Jun. 17, 2003

(54) BIOLOGICAL SPECIMEN HEATING DEVICE AND QUALITY CONTROL METHOD FOR IMMUNOHISTOCHEMISTRY HEAT RETRIEVAL PROCEDURES

(75) Inventor: David Tacha, Martines, CA (US)

(73) Assignee: BioCare Medical, Walnut Creek, CA (US)

( * ) Notice: Subject to any disclaimer, the term of this patent is extended or adjusted under 35 U.S.C. 154(b) by 123 days.

(21) Appl. No.: 09/961,043

(22) Filed: Sep. 21, 2001

(51) Int. Cl.[7] .................... F27B 14/20; G01N 33/53; G01N 33/574; F27D 19/00
(52) U.S. Cl. ................ 219/440; 219/442; 73/54.42; 73/54.43; 435/7.23; 435/960
(58) Field of Search ................ 219/437, 440, 219/441, 442; 73/53.01, 54.42, 54.43; 435/7.23, 34, 960, 970

(56) References Cited

U.S. PATENT DOCUMENTS 5,444,218 A * 8/1995 Zelniker et al. ............ 219/440
5,567,458 A * 10/1996 Wu ............................ 219/441
5,842,353 A * 12/1998 Kuo-Liang ................. 219/441
6,173,643 B1 * 1/2001 Qian et al. .................. 219/440
6,283,014 B1 * 9/2001 Ng et al. .................... 219/440
6,303,323 B1 * 10/2001 Laskey et al. ............. 435/7.23
6,391,624 B1 * 5/2002 Megerle .................... 422/68.1

* cited by examiner

Primary Examiner—Joseph Pelham
(74) Attorney, Agent, or Firm—Jack Lo

(57) ABSTRACT

A heating device for heating biological specimens is comprised of an electric pressure cooker with a pressure gauge, and a temperature sensor connected to a controller with a temperature display and a temperature alert. The controller is arranged to heat the specimen at a selectable temperature for a selectable time period. The quality control process is comprised of placing in the cooker a heat sensitive pH indicating retrieval solution, and a heat and pressure sensitive steam strip. When the set temperature has been reached, the actual temperature and pressure are recorded. When the cooker is opened after heating, the pH indicating solution is checked for color change that indicates a pH change, and the steam strip is checked for color change that indicates predetermined temperature and pressure levels have been reached.

9 Claims, 4 Drawing Sheets

BIOLOGICAL SPECIMEN HEATING DEVICE AND QUALITY CONTROL METHOD FOR IMMUNOHISTOCHEMISTRY HEAT RETRIEVAL PROCEDURES

BACKGROUND OF THE INVENTION

1. Field of the Invention

This invention relates generally to methods and apparatus for heating biological specimens.

2. Prior Art

Medical analysis of human or animal tissue specimens comprises embedding the specimens in paraffin, cutting thin slices from the paraffin blocks, and placing the slices on microscope slides. The specimens are stained for improved viewing under a microscope. For further analysis, immunohistochemistry or similar techniques may be used, wherein monoclonal or polyclonal antibodies are used to identify tumors, infectious diseases, tissue constituents, etc. Some of the specimens may require the application of a heat retrieval method to permit the antibodies or probes access to the targeted antigen/epitope or sequence. The heat retrieval method comprises placing a retrieval solution on the slides, and heating the slides to between 80 and 120 degrees C. in a heating device such as a microwave, steamer, rice cooker, pressure cooker, or autoclave. Using a pressure cooker raises the boiling point of the solution and prevents it from boiling off at maximum cooker temperature, and also speeds up the process. After heating, the slides are removed from the heating device for immunohistochemistry analysis.

A major problem with heating slides in a conventional cooking device such as a microwave or pressure cooker is that the temperature and pressure cannot be monitored for precise and reliable results. According to laboratory governing bodies that issue operating standards for quality control, such as the College of American Pathologists (CAP), daily quality control measures should be implemented for such laboratory testing. Typical guidelines issued by a governing body are as follows:

1. Laboratory tests using a heating device should be have the temperature recorded.
2. Laboratory tests using pressure should have the pressure recorded.
3. The pH of solutions for heat retrieval procedures should be recorded at the temperature used.
4. Any electrical water bath should have a 3-prong power plug.

Conventional cooking devices cannot measure temperature, pressure, or pH. A tissue slide heating device which can measure pressure is sold under the trademark "DECLOAKING CHAMBER DC2000" by BioCare Medical of Walnut Creek, Calif. However, it does not measure temperature, so that it cannot be used for complying with laboratory quality control standards. Another problem is that it does not automatically adjust the total heating time to compensate for different amounts of materials in the cooker, since more massive contents must be heated longer than less contents.

OBJECTIVES OF THE INVENTION

The objectives of the present biological specimen heating device and quality control method are:

to heat biological specimens to a selectable temperature;
to heat the specimens under pressure;
to automatically adjust the total heating time to compensate for different amounts of materials;
to enable recording of the actual temperature inside the cooker for quality control;
to enable recording of the actual pressure inside the cooker for quality control;
to enable recording of the pH of the retrieval solutions at the set temperature for quality control;
to accurately indicate the pH of the retrieval solutions at the set temperature;
to provide redundancy in pH indication for reliability;
to provide redundancy in pressure indication for reliability; and
to increase safety.

Further objectives of the present invention will become apparent from a consideration of the drawings and ensuing description.

BRIEF SUMMARY OF THE INVENTION

A heating device for heating biological specimens is comprised of an electric pressure cooker with a pressure gauge, and a temperature sensor connected to a controller with a temperature display and a temperature alert. The controller is arranged to heat the specimen at a selectable temperature for a selectable time period. The quality control process is comprised of placing in the cooker a heat sensitive pH indicating retrieval solution, and a heat and pressure sensitive steam strip. When the set temperature has been reached, the actual temperature and pressure are recorded. When the cooker is opened after heating, the pH indicating solution is checked for color change that indicates a pH change, and the steam strip is checked for color change that indicates predetermined temperature and pressure levels have been reached.

DETAILED DESCRIPTION OF THE INVENTION

Figure 1:
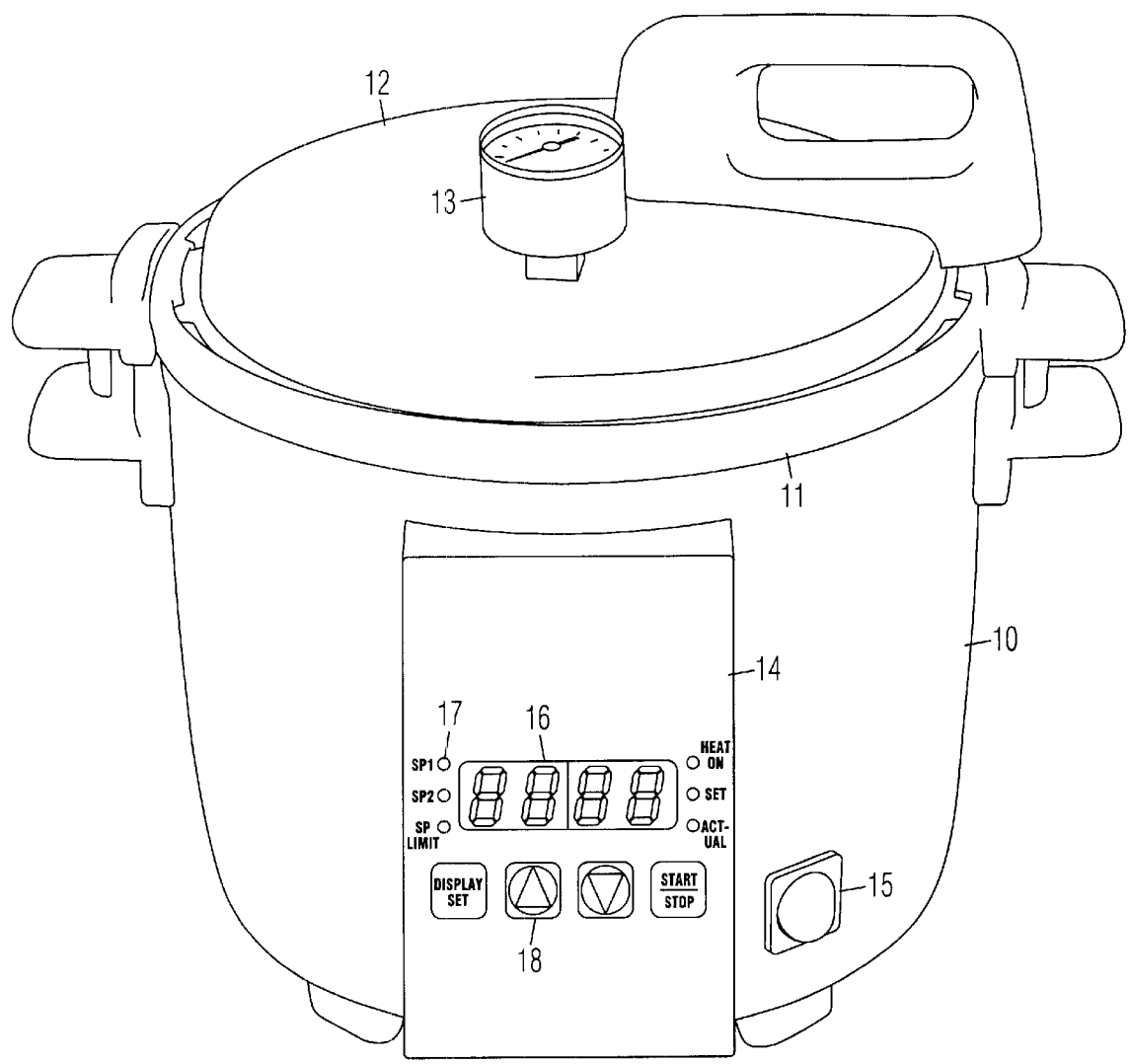
FIG. 1 is a front perspective view of the present heating device.

FIG. 1:

A preferred embodiment of the present biological specimen heating device for immunohistochemistry procedures is shown in a front perspective view in FIG. 1. It is comprised of an electric pressure cooker 10 with a pressure chamber 11 (only the top rim is shown), a removable lid 12 covering pressure chamber 11, a pressure gauge 13 attached to lid 12, a controller 14 attached to a front side, and a power switch 15 attached to the front side. Pressure cooker 10 is preferably of the type used for cooking, such as any of the Panasonic models, but it may be comprised of any other suitable type of pressure heating device. Pressure gauge 13 is communicably connected to an internal surface of lid 12 for sensing the pressure inside cooker, and is preferably calibrated to read from about 0 psi to at least about 30 psi. Controller 14 is arranged to control and display cooker temperature, and control heating time. Controller 14 is preferably comprised of a digital controller, although an analog controller may be provided. Controller 14 includes a display 16, indicator lights 17, and a keypad 18. Controller 14 thus integrates a temperature control, a timer control, and a temperature display.

Figure 2:
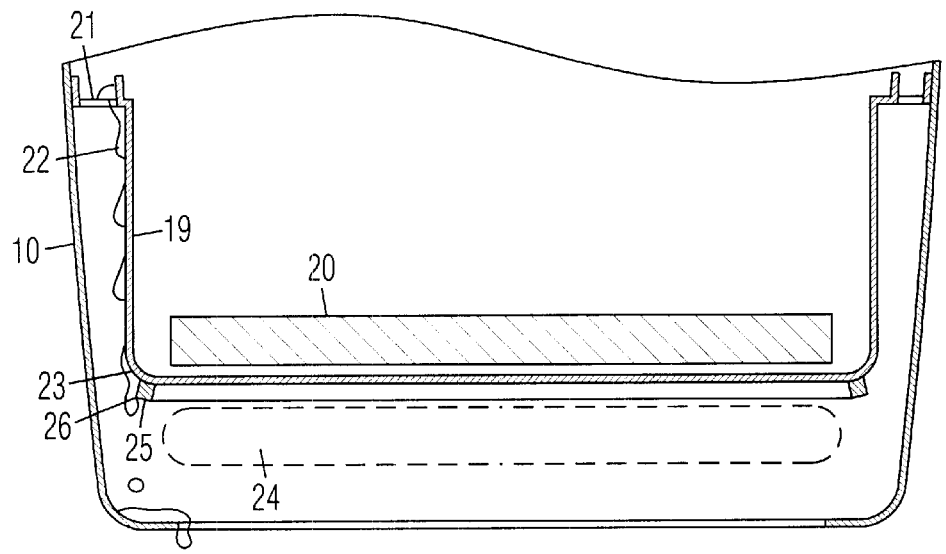
FIG. 2 is a sectional view of a drip skirt thereof.
Figure 3:
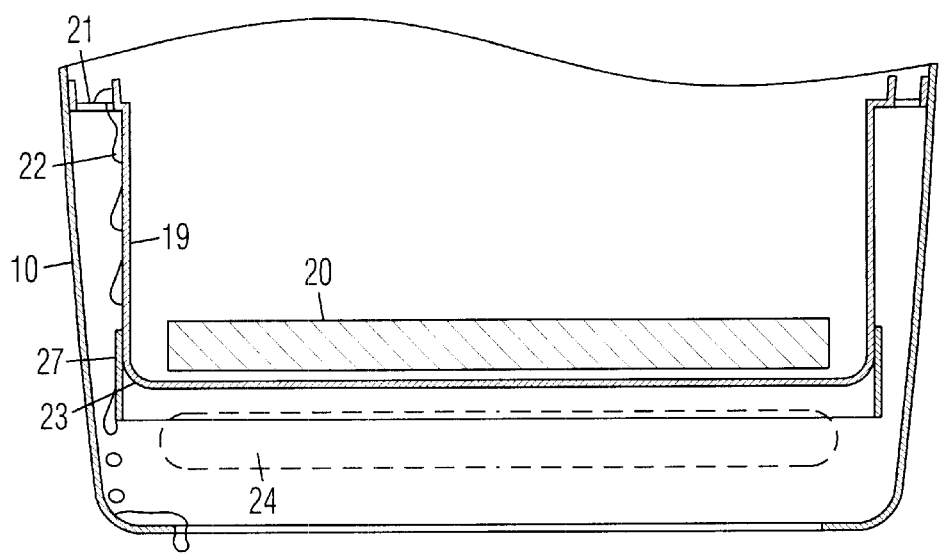
FIG. 3 is a sectional view of an alternative drip skirt thereof.

FIGS. 2–3:

The heating device is shown in a sectional view in FIG. 2. Pressure cooker 10 has a deeply concave inner pan 19 with a heating element 20 positioned at an inner bottom, and louvers 21 around a top rim for ventilation. Fluids 22 condensed from steam often drips onto louvers 21 when the lid is opened. Fluid 22 dripping down the side of inner pan 19 can flow around a large radius bottom corner or rim 23 thereof onto an electrical wiring area 24 and pose a shorting hazard. Therefore, a drip skirt 25 with a sharp corner or rim 26 is attached all around bottom corner or rim 23 of inner pan 19 to prevent dripping fluid 22 from rounding corner or rim 23. In a first embodiment shown in FIG. 2, drip skirt 25 is comprised of a rectangular strip of temperature resistant material such as an adhesive backed silicone rubber strip. Other suitable types of materials may be used, such as "VITON", "TEFLON", or metal. In a second embodiment shown in FIG. 3, a drip skirt 27 is comprised of a tubular skirt attached around inner pan 19 and projecting below bottom corner or rim 23. In either embodiment, the drip skirt should be made of a material which can withstand temperatures of least about 150 degree C.

Figure 4:
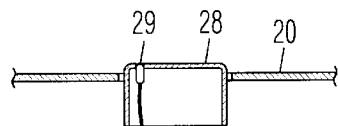
FIG. 4 is a sectional view of a temperature sensor thereof.

FIG. 4:

A sectional view of a sensor button 28 in heating element 20 is shown in FIG. 4. Sensor button 28 is a common feature in many pressure cookers and rice cookers. The pressure chamber (not shown) is typically positioned on top of sensor button 28. A temperature sensor 29 is attached to sensor button 28, preferably inside a hole extending through a top surface of sensor button 28.

Figure 5:
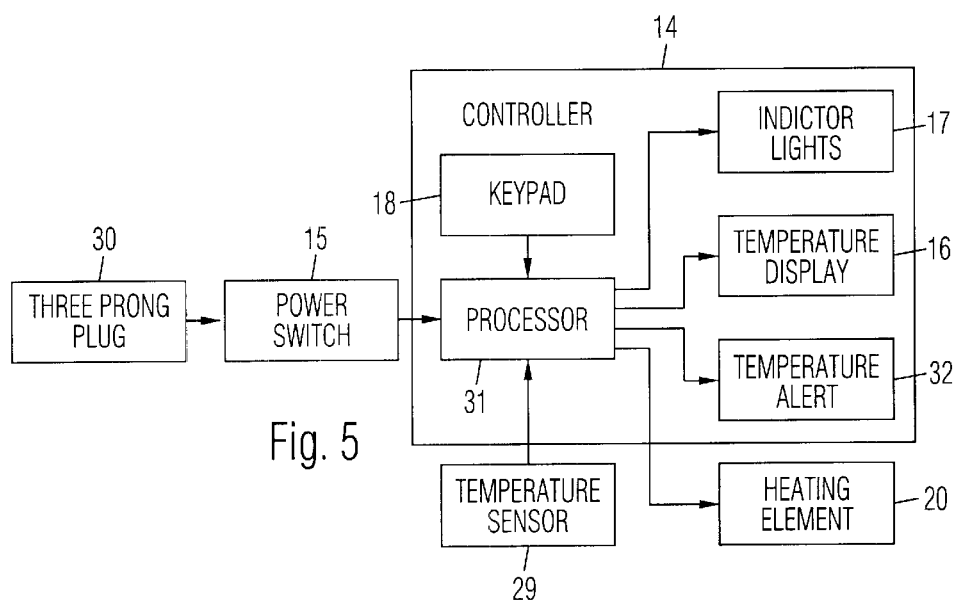
FIG. 5 is a schematic block diagram of the heating device.

FIG. 5:

A schematic block diagram of the heating device is shown in FIG. 5. A three-prong plug 30 that includes a ground connector is provided for meeting laboratory governing body operating standards. Plug 30 is connected to power switch 15 which provides power to controller 14. Controller 14 is comprised of a processor 31 connected to keypad 18, indicator lights 17, display 16, a temperature alert 32, temperature sensor 29, and heating element 20. Temperature alert 32 may be an audio and/or visual alert.

Figure 6:
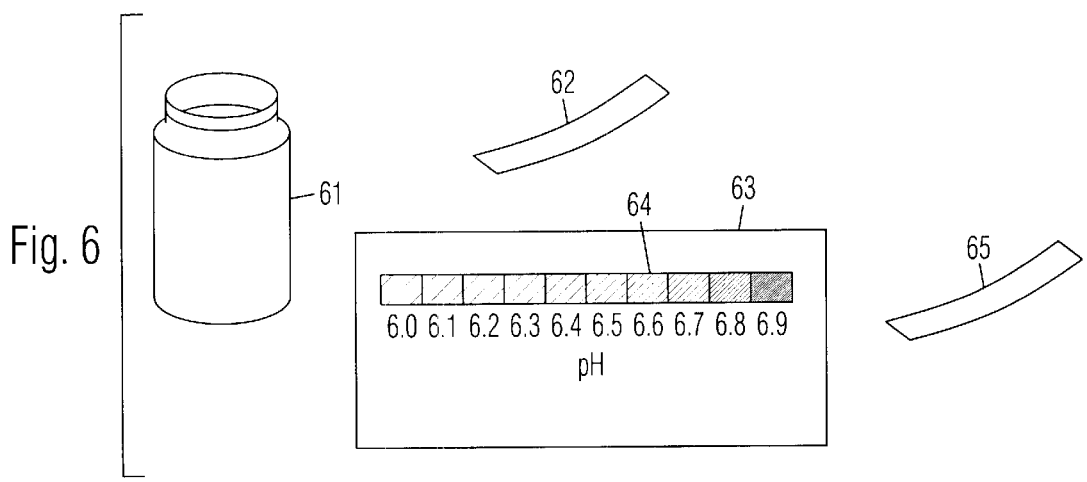
FIG. 6 is a front view of quality control devices used with the heating device.

FIG. 6:

As shown in FIG. 6, quality control devices for use with the present heating device includes a first pH indicator or pH indicating retrieval solution 61, a second pH indicator or pH strip 62, a heat adjusted color chart 63 with a temperature adjusted color range 64, and a heat and pressure sensitive steam strip 65. The use of these device are disclosed in conjunction with FIG. 8.

Figure 7:
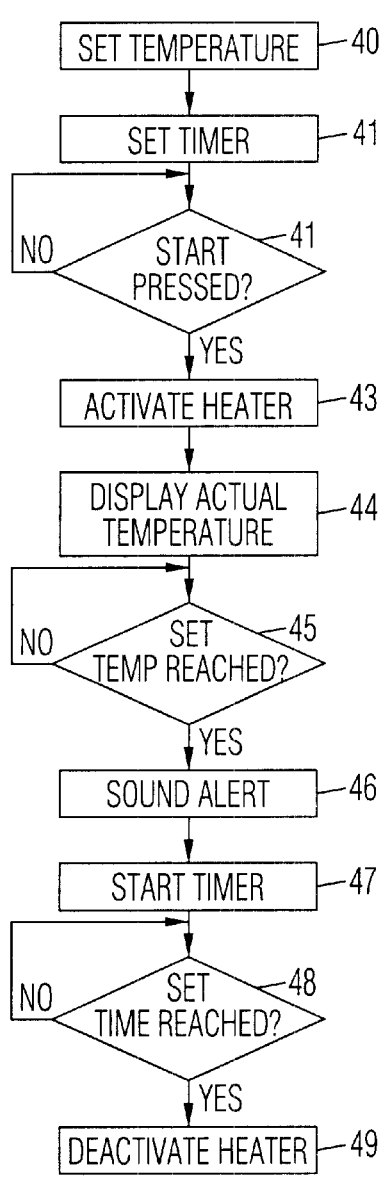
FIG. 7 is a flowchart of the operation of a controller thereof.

FIG. 7:

The programming and operation of the controller is shown in a flowchart in FIG. 7. After power up, the maximum cooker temperature is set at step 40, and the timer is set at step 41. When the start button is pressed at step 42, the heating element is activated at step 43. The actual temperature measured by the temperature sensor is continuously updated and displayed at step 44. When the set temperature is reached at step 45, the timer is started at step 46 to maintain the set temperature for the set duration. When the timer expires at step 47, the temperature alert is sounded at step 48, and the heating element is deactivated at step 49. The actual temperature is continually displayed and updated even after the timer expires. Since more massive materials require longer a heating time to reach the set temperature and vice versa, starting the timer after the set temperature has been reached automatically adjusts the total heating time to compensate for the mass of the materials being heated.

Alternatively, the processor may be arranged to enable the setting of a plurality of set points, wherein each set point is comprised of a temperature and timer duration. When the start button is pressed, the heating element will be activated until the first set point has been reached, and then deactivated. When the start button is pressed again without turning off the controller, the heating element will be activated again until a second set point has been reached, and so forth. The first set point may be a maximum temperature, and the second set point may be a keep-warm temperature. The second set point may also be a cooling down period in which the temperature is set at 0 to keep the heating element turned off. When the second set point has been reached, the alert is sounded to notify the user that the cooker has cooled and depressurized enough to be opened safely.

Figure 8:
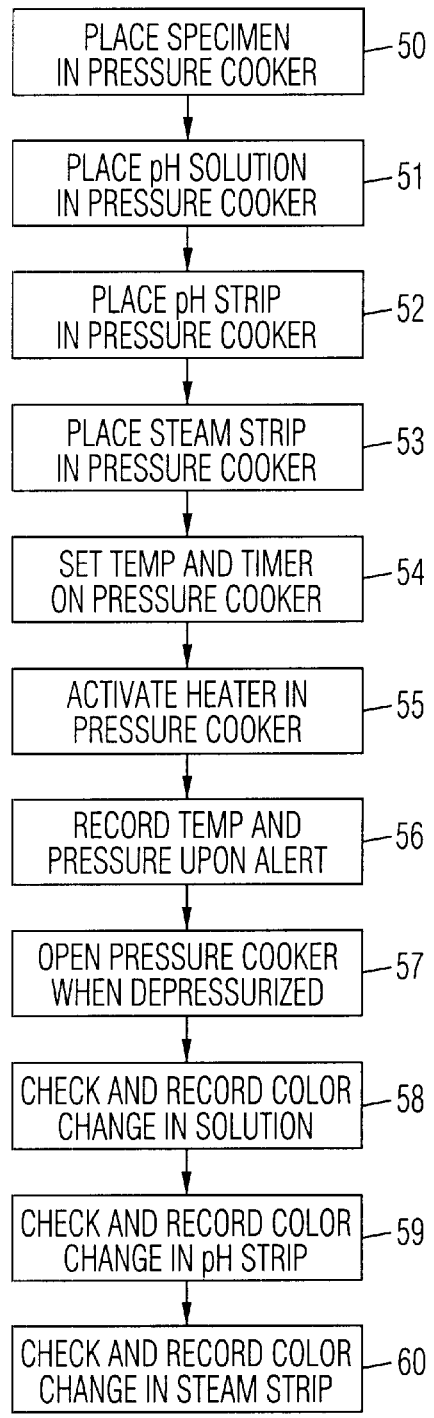
FIG. 8 is a flowchart of a quality control process for using the heating device.

FIG. 8:

To comply with laboratory governing body operating regulations, such as CAP guidelines, the present invention includes a quality control method for using the heating device in the flowchart in FIG. 8. A small container of heat sensitive pH indicating retrieval solution is placed in the pressure cooker at step 50. The biological specimen is placed in the pH indicating retrieval solution at step 51. Alternatively, the specimen can be placed in a non-pH indicating retrieval solution, but the pH strip may be used instead as described below.

The pH indicating retrieval solution is arranged to change color at a predetermined temperature range to indicate pH change. The preferred pH indicating retrieval solution are sold under the trademarks "REVEAL" and "BORGDE-CLOAKER" by BioCare Medical of Walnut Creek, Calif. The "REVEAL" retrieval solution is arranged to change from a yellow color at room temperature and a pH of 6.0 to an orange color at between about 80–125 degrees C. to indicate a pH range of about 6.4 to 6.5. The "BORGDE-CLOAKER" retrieval solution is arranged to change from a lavender color at room temperature at a pH of 9.5 to a gray color at between about 80–125 degrees C. to indicate a pH range of about 8.4 to 8.6. Since the pH of the pH indicating retrieval solution changes at the elevated temperature range of 80–125 degrees C., the color change represents a corresponding pH change. The pH ranges of the "REVEAL" and "BORGDECLOAKER" retrieval solutions are narrow enough for accuracy.

A heat and pressure sensitive steam strip is placed in the pressure cooker at step 52. The steam strip is preferably arranged to change from a white color at room temperature to a dark charcoal color when heated to about 120 degrees C. at about 17–25 psi for 2–3 minutes. The steam strip thus backs up the readings of the temperature sensor and pressure gauge, and also to provide redundancy for reliability.

The maximum heating temperature and timer on the controller are set at step 53. For "REVEAL" and "BORG- DECLOAKER" solutions, the temperature preferably set to about 120 degrees C. and the timer is preferably set to about 2–3 minutes. The heating is initiated at step 54. When the set temperature is reached and the temperature alert is sounded, the user records the actual temperature shown on the display, which may vary from the set temperature, and records the actual pressure shown on the pressure gauge at step 55. Typical pressure is between about 17–25 psi. This fulfills the recording temperature and pressure recording requirements of governing body regulations. The cooker can be safely opened after the pressure has reached 0. After the cooker is opened at step 56, the color of the pH indicating solution is checked and recorded at step 57 for the proper color change which indicates that a predetermined pH has been reached.

If a non-pH indicating retrieval solution is used, for example, because of user preference, a pH strip may be placed in the retrieval solution at step 58. Step 57 is skipped if the non-pH indicating retrieval solution is used. As a backup and to provide redundancy for reliability, the pH strip may also be placed in a pH indicating retrieval solution, in which case steps 57–59 are all used.

In a conventional pH strip system, a color chart calibrated for room temperature testing is provided. However, heating a pH strip turns it darker than at room temperature for the same pH change. If the pH strip in the cooker is matched with a conventional color chart after heating, the chart will indicate a higher pH, when the actual pH is lower. Since the color change of the pH strip is different at elevated temperatures than at room temperature, a heat adjusted color chart is provided. The heat adjusted color chart has a color range which is darkened to compensate for the darkening effect of the heat, and is thus arranged to accurately measure pH at between about 80–125 degrees C. of the present heating process.

If the pH strip is used instead or concurrently, it is compared to the heat adjusted color chart to read and record the actual pH reached at step 59. The pH strip can also be used with other types of retrieval solutions, whether home-brewed or commercial solutions, which do not change color at elevated temperatures. The actual pH is recorded to fulfill the pH recording requirement of governing body regulations.

The heat and pressure sensitive steam strip is also checked at step 60 for the proper color change which indicates that a predetermined temperature and pressure have been reached. This backs up the reading of the digital temperature display and the pressure gauge for reliability and accuracy.

SUMMARY AND SCOPE

Accordingly, the present heating device is arranged to heat biological specimens to a selectable temperature. It heats the specimens under pressure. It activates an alert when the set temperature has been reached to notify the user record to the actual temperature for quality control as required by laboratory governing body operating standards. It automatically adjusts the total heating time to compensate for different amounts of materials. It enables recording of the actual pressure inside the cooker for quality control. It enables recording of the pH of the specimens at the set temperature for quality control. It accurately indicates the pH of the specimens at the set temperature. It provides redundancy in pH indication, temperature indication, and pressure indication for reliability. It also increases safety.

Although the foregoing description is specific, it should not be considered as a limitation on the scope of the invention, but only as an example of the preferred embodiment. Many variations are possible within the teachings of the invention. For example, different attachment methods, fasteners, materials, dimensions, etc. can be used unless specifically indicated otherwise. The relative positions of the elements can vary, and the shapes of the elements can vary. Therefore, the scope of the invention should be determined by the appended claims and their legal equivalents, not by the examples given.

I claim:

1. A biological specimen heating device, comprising:
   an electric pressure cooker;
   a heating element in said cooker;
   a pressure chamber in said cooker arranged for receiving a biological specimen and producing a predetermined pressure;
   a pressure gauge attached to said pressure chamber;
   a temperature sensor in said cooker arranged for measuring a temperature of said pressure chamber; and
   a controller with a temperature display, wherein said controller is connected to said heating element and said temperature sensor, and is arranged to activate said heating element, display an actual temperature measured by said temperature sensor for quality control, and maintain said pressure chamber at a selectable temperature for a selectable timer period.

2. The biological specimen heating device of claim 1, further including a temperature alert in said controller, wherein said controller is arranged to activate said temperature alert when said selectable temperature is reached.

3. The biological specimen heating device of claim 1, further including:
   a concave inner pan with a rounded bottom corner inside said cooker; and
   an annular drip skirt with a sharp lower corner attached around a lower side of said bottom corner of said inner pan for preventing any dripping fluid from flowing under said rounded corner of said inner pan and onto an electrical wiring area.

4. The biological specimen heating device of claim 1, wherein said selectable temperature is within a range of about 80–125 degrees C., and further including quality control devices for being positioned inside said cooker for helping meet predetermined laboratory governing body quality control regulations, wherein said quality control devices comprise a heat and pressure sensitive steam strip arranged to change color at said selectable temperature and said pressure for indicating temperature and pressure changes, and a pH indicating solution arranged to change color at said selectable temperature for indicating a pH change to a value within a predetermined range of pH.

5. The biological specimen heating device of claim 1, wherein said selectable temperature is within a range of about 80–125 degrees C., and further including quality control devices for being positioned inside said cooker for helping meet predetermined laboratory governing body quality control regulations, wherein said quality control devices comprise a heat and pressure sensitive steam strip arranged to change color at said selectable temperature and said pressure for indicating temperature and pressure changes, a pH strip arranged to change color at said selectable temperature for indicating a pH change to a value within a predetermined range of pH, and a heat adjusted color chart arranged for accurately reading said pH strip after said pH strip is heated to said selectable temperature.

6. A quality controlled method for heating a laboratory biological specimen, comprising the steps of:

placing a heat sensitive pH indicating retrieval solution in a pressure cooker with a temperature control, a timer control, a temperature display, and a pressure gauge, wherein said cooker is operable within a predetermined temperature range and a predetermined pressure range, and is arranged to display an actual temperature, wherein said pH indicating retrieval solution is arranged for changing color within said temperature range to indicate a pH change to a value within predetermined range of pH;

placing said biological specimen in said pH indicating retrieval solution;

setting a heating temperature with said temperature control;

setting a timer period with said timer control;

activating said cooker;

recording an actual temperature shown on said temperature display and an actual pressure shown on said pressure gauge after said heating temperature is reached;

opening said cooker after heating;

checking said pH indicating retrieval solution for color change which indicates that said range of pH has been reached; and recording pH indicated by said pH indicating retrieval solution.

7. A quality controlled method for heating a laboratory biological specimen, comprising the steps of:

placing a heat sensitive pH indicating retrieval solution in a pressure cooker with a temperature control, a timer control, a temperature display, and a pressure gauge, wherein said cooker is operable within a predetermined temperature range and a predetermined pressure range, and is arranged to display an actual temperature, wherein said pH indicating retrieval solution is arranged for changing color within said temperature range to indicate a pH change to a value within predetermined range of pH;

placing said biological specimen in said pH indicating retrieval solution;

placing a heat and pressure sensitive steam strip in said cooker, wherein said steam strip is arranged to change color within said temperature range and said pressure range for indicating temperature and pressure changes;

setting a heating temperature with said temperature control;

setting a timer period with said timer control;

activating said cooker;

recording an actual temperature shown on said temperature display and an actual pressure shown on said pressure gauge after said heating temperature is reached;

opening said cooker after heating;

checking said pH indicating retrieval solution for color change which indicates that said range of pH has been reached;

recording pH indicated by said pH indicating retrieval solution; and checking said steam strip for color change which indicates that said temperature range and said pressure range have been reached, so as to back up reading of said temperature display and said pressure gauge for reliability and accuracy.

8. A quality controlled method for heating a laboratory biological specimen, comprising the steps of:

placing a retrieval solution in a pressure cooker with a temperature control, a timer control, a temperature display, and a pressure gauge, wherein said cooker is operable within a predetermined temperature range and a predetermined pressure range, and is arranged to display an actual temperature;

placing said biological specimen in said retrieval solution;

setting a heating temperature with said temperature control;

setting a timer period with said timer control;

activating said cooker;

recording an actual temperature shown on said temperature display and an actual pressure shown on said pressure gauge after said heating temperature is reached;

opening said cooker after heating;

placing a pH strip in said retrieval solution;

comparing said pH strip to a heat adjusted color chart arranged for accurately reading said pH strip after said pH strip is heated by said retrieval solution; and recording pH indicated by said pH strip.

9. A quality controlled method for heating a laboratory biological specimen, comprising the steps of:

placing a retrieval solution in a pressure cooker with a temperature control, a timer control, a temperature display, and a pressure gauge, wherein said cooker is operable within a predetermined temperature range and a predetermined pressure range, and is arranged to display an actual temperature;

placing said biological specimen in said retrieval solution;

placing a heat and pressure sensitive steam strip in said cooker, wherein said steam strip is arranged to change color within said temperature range and said pressure range for indicating temperature and pressure changes;

setting a heating temperature with said temperature control;

setting a timer period with said timer control;

activating said cooker;

recording an actual temperature shown on said temperature display and an actual pressure shown on said pressure gauge after said heating temperature is reached;

opening said cooker after heating;

placing a pH strip in said retrieval solution;

comparing said pH strip to a heat adjusted color chart arranged for accurately reading said pH strip after said pH strip is heated by said retrieval solution;

recording pH indicated by said pH strip; and checking said steam strip for color change which indicates that said temperature range and said pressure range have been reached, so as to back up reading of said temperature display and said pressure gauge for reliability and accuracy.

* * * * *